(12) United States Patent
Tsai et al.

(10) Patent No.: US 10,039,453 B2
(45) Date of Patent: Aug. 7, 2018

(54) OPTICAL DETECTING MODULE WITH WATERPROOFING FUNCTION

(71) Applicant: PixArt Imaging Inc., Hsin-Chu (TW)

(72) Inventors: Cheng-Nan Tsai, Hsin-Chu (TW);
Hung-Ching Lai, Hsin-Chu (TW);
Chih-Yuan Chuang, Hsin-Chu (TW);
Hung-Yu Lai, Hsin-Chu (TW);
Yung-Chang Lin, Hsin-Chu (TW);
Yi-Min Liu, Hsin-Chu (TW); Ren-Hau Gu, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 192 days.

(21) Appl. No.: 14/720,845

(22) Filed: May 25, 2015

(65) Prior Publication Data

US 2016/0150960 A1 Jun. 2, 2016

(30) Foreign Application Priority Data

Nov. 27, 2014 (TW) .............................. 103141273 A
Mar. 16, 2015 (TW) .............................. 104108342 A

(51) Int. Cl.
*A61B 5/18* (2006.01)
*A61B 5/00* (2006.01)

(52) U.S. Cl.
CPC .......... *A61B 5/0059* (2013.01); *A61B 5/6801* (2013.01); *A61B 2562/18* (2013.01)

(58) Field of Classification Search
CPC .. A61B 5/0059; A61B 5/6801; A61B 2562/18
See application file for complete search history.

(56) References Cited

U.S. PATENT DOCUMENTS

2014/0135612 A1* 5/2014 Yuen .................. A61B 5/02405
600/407
2014/0361147 A1* 12/2014 Fei ........................ G01J 1/0407
250/206

* cited by examiner

*Primary Examiner* — Rex R Holmes
(74) *Attorney, Agent, or Firm* — Winston Hsu

(57) ABSTRACT

An optical detecting module with waterproofing function can be installed on a housing of a wearable device and includes an optical detecting component, a light source and a packaging structure. The light source is disposed by the optical detecting component, and the packaging structure provides the waterproofing function to the optical detecting component and the light source. The packaging structure includes a main body, a light emitting unit, a light incoming unit and a waterproofing component. The main body covers the optical detecting component and the light source. The light emitting unit and the light incoming unit are disposed on the main body and respectively face the light source and the optical detecting component. The waterproofing component is filled into a gap formed between the main body and the housing, to prevent moisture from leaking into the gap to rust terminals of the optical detecting component and the light source.

9 Claims, 3 Drawing Sheets

OPTICAL DETECTING MODULE WITH WATERPROOFING FUNCTION

BACKGROUND OF THE INVENTION

1. Field of the Invention

The present invention relates to an optical detecting module, and more particularly, to an optical detecting module applied to a wearable device and having waterproofing function.

2. Description of the Prior Art

With the advanced technology, the wearable device can be the time clock with physiological characteristics detecting function to immediately detect health status of the human body. The wearable device usually utilizes an optical detecting module to detect the physiological characteristics. However, the conventional optical detecting module does not have sufficient waterproofing function, and inner electronic components of the optical detecting module may be damaged or rusted easily due to leakage of exterior moisture. Design of an optical detecting module with small size and having perfect waterproofing function is an important issued in the mechanism design industry.

SUMMARY OF THE INVENTION

The present invention provides an optical detecting module applied to a wearable device and having waterproofing function for solving above drawbacks.

According to the claimed invention, an optical detecting module with waterproofing function capable of being installed on a housing of a wearable device is disclosed. The optical detecting module includes an optical detecting component, a light source disposed adjacent by the optical detecting component, and a packaging structure adapted to protect the optical detecting component and the light source by the waterproofing function. The packaging structure includes a main body, a light emitting unit, a light incoming unit and a waterproofing component. The main body covers the optical detecting component and the light source. The light emitting unit is disposed on the main body and faces the light source. The light incoming unit is disposed on the main body and faces the optical detecting component. The waterproofing component is filled into a gap formed between the main body and the housing, so as to prevent exterior moisture from leaking into the gap to rust terminals of the optical detecting component and/or the light source.

According to the claimed invention, the main body includes an inner surface and an outer surface opposite to each other. The optical detecting component and the light source are surrounded and covered by the inner surface of the main body, and opposite sides of the waterproofing component are respectively disposed on the housing and the outer surface. The packaging structure further includes at least one blocking component disposed between the optical detecting component and the light source, and/or between the light emitting unit and the light incoming unit.

According to the claimed invention, the main body includes a covering portion and a bridging portion, the optical detecting component and the light source are located inside a sunken space of the covering portion, and the bridging portion is connected to an outer of the covering portion. The waterproofing component is disposed between the housing and the bridging portion, and/or between the housing and the covering portion. The bridging portion stretches out from the covering portion. The housing includes a suspending component, the packaging structure is disposed inside an opening formed on the suspending component, and the waterproofing component is disposed between the bridging portion and the suspending component.

According to the claimed invention, the light emitting unit and the light incoming unit are disposed on a top of the main body, and a distance between the top and an opening formed on the housing is at least greater than 0.3 mm. The packaging structure further includes a first light transmissive unit and a second light transmissive unit, the first light transmissive unit is disposed between the light source and the light emitting unit, and the second light transmissive unit is disposed between the optical detecting component and the light incoming unit. The optical detecting component and the light source are respectively packed inside the packaging structure, or are integrated inside the packaging structure monolithically. The main body is an arc shape cylinder or a polygonal cylinder.

The present invention provides the optical detecting module matched with the housing of the wearable device for the waterproofing function. The waterproofing component of the optical detecting module is disposed between the suspending component of the housing and the covering portion/the bridging portion of the main body. The main body can be the arc shape such as the circular form or the elliptical form, and the waterproofing component is disposed around the arc shape of the main body. The main body further can be the polygonal shape such as the rectangle form, and the waterproofing component is disposed on sides of the main body accordingly. It should be mentioned that the optical detecting module has the light emitting unit and the light incoming unit disposed on a top of the main body, a distance between the top and the opening is at least greater than 0.3 mm to overcome assembly tolerance, and the optical detecting module can actually contact against the human body to detect the accurate physiological characteristics. Comparing to the prior art, the present invention effectively increase the waterproofing function of the optical detecting module applied to the wearable device, the terminals of the optical detecting component and the light source are not damaged by sweat of the human body, and the wearable device can be suitable for outdoor activity and water activity.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
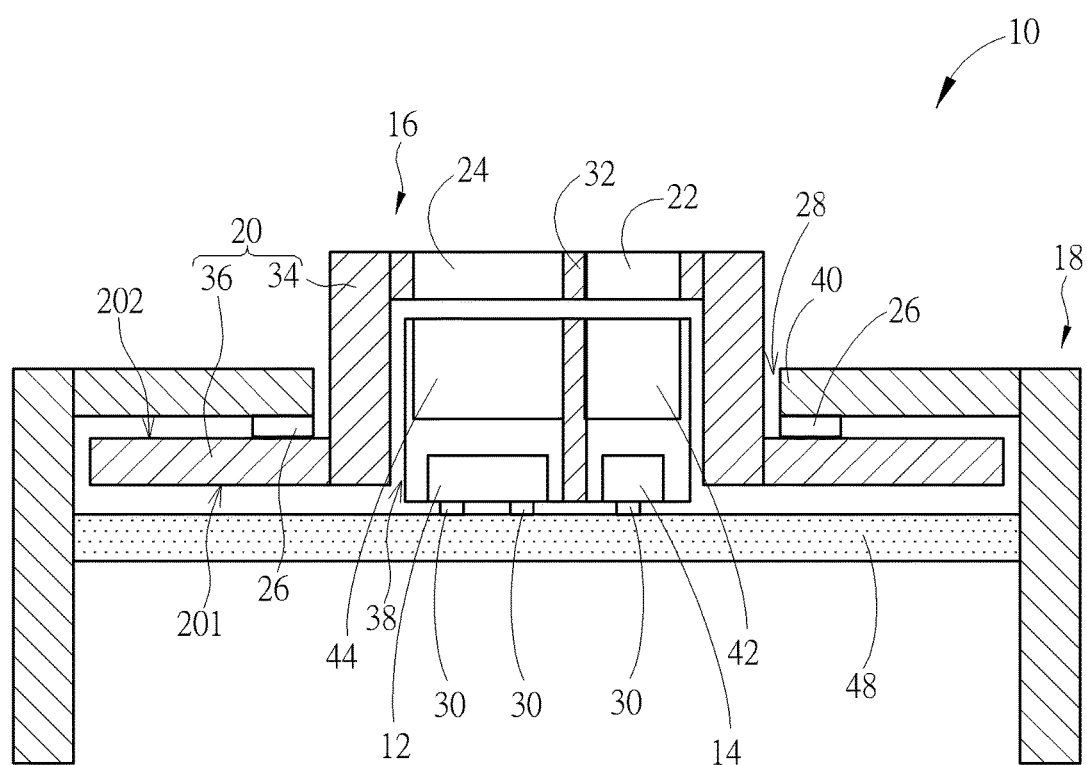
FIG. 1 is a sectional view of an optical detecting module according to a first embodiment of the present invention.

Please refer to FIG. 1. FIG. 1 is a sectional view of an optical detecting module 10 according to a first embodiment of the present invention. The optical detecting module 10 has a small volume and is suitable for being installed on a wearable device. The wearable device can be the smart phone or the smart wristband. While the wearable device is wore on the human body, the optical detecting module can utilize visible light or invisible light to detect physiological characteristics of the human body, such as contraction of the vessel, and the wearable device can generate feedback according to the detected physiological characteristics immediately. Therefore, the optical detecting module 10 has to provide sufficient waterproofing function to prevent external moisture from leaking into the wearable device, so as to avoid the detecting function of the optical detecting module 10 from damage.

The optical detecting module 10 includes an optical detecting component 12, a light source 14 and a packaging structure 16. The light source 14 emits a detective light, the optical detecting component 12 receives a reflective light reflected from the human body by the detective light, and the reflective light can be analyzed to acquire the related physiological characteristics. The optical detecting component 12 is preferably close to the light source 14 to minimize the size of the optical detecting module 10. For preventing the external moisture from leaking into the wearable device, the optical detecting module 10 disposes the packaging structure 16 on a position between the housing 18 of the wearable device and the optical detecting component 12 and the light source 14 to provide the waterproofing function. The packaging structure 16 includes a main body 20, a light emitting unit 22, a light incoming unit 24 and a waterproofing component 26. Shape of the main body 20 can be, but not limited to, an arc shape cylinder or a polygonal cylinder. Any structure capable of completely covering the optical detecting component 12 and the light source 14 and inserting into an opening 28 on the housing 18 belongs to a scope of the main body 20 illustrated in the present invention.

The main body 20 includes an inner surface 201 and an outer surface 202 opposite to each other. The optical detecting component 12 and the light source 14 are surrounded and covered by the inner surface 201 of the main body 20, and two opposite sides of the waterproofing component 26 are respectively disposed on the housing 18 and the outer surface 202. The optical detecting component 12 and the light source 14 can be isolated from an exterior environment where the wearable device is located by the main body 20 and the waterproofing component 26 of the packaging structure 16.

The light emitting unit 22 and the light incoming unit 24 can be light transmissive components or transparent components respectively disposed on different positions of the main body 20. The light emitting unit 22 faces the light source 14, the light incoming unit 24 faces the optical detecting component 12, the detective light generated by the light source 14 can be projected onto the human body through the light emitting unit 22, and the related reflective light can pass through the light incoming unit 24 to be received by the optical detecting component 12. In this embodiment, the optical detecting component 12 and the light source 14 are integrated with a circuit board 48 monolithically, and a first light transmissive unit 42 and a second light transmissive unit 44 are disposed accordingly. The first light transmissive unit 42 is disposed between the light source 14 and the light emitting unit 22, the second light transmissive unit 44 is disposed between the optical detecting component 12 and the light incoming unit 24, and the first light transmissive unit 42 and the second light transmissive unit 44 are utilized as light guiding components. The waterproofing component 26 is filled into a gap formed between the main body 20 and the housing 18, to prevent the exterior moisture from leakage to rust terminals 30 of the optical detecting component 12 and/or the light source 14.

The packaging structure 16 further can include at least one blocking component 32 disposed between the optical detecting component 12 and the light source 14, and/or between the light emitting unit 22 and the light incoming unit 24, to make the optical detecting component 12 only receive the reflective light through the light incoming unit 24 without noise interference. The blocking component 32 is made of opaque material to prevent the optical detecting component 12 from being interfered by the detective light of the light source 14 through an inner path of the optical detecting module 10. The blocking component 32 not only can be the physical light isolating component as mentioned above, but also can be an air gap formed between the optical detecting component 12 and the light source 14, and/or between the light emitting unit 22 and the light incoming unit 24. While the detective light generated by the light source 14 is projected on to a surface of the air gap, the detective light cannot pass through the air gap due to total internal reflection and the optical detecting component 12 can be effectively protected without light interference.

The main body 20 may include a covering portion 34 and a bridging portion 36 connected to each other. The covering portion 34 has a sunken space 38 where inside the optical detecting component 12 and the light source 14 are disposed. The bridging portion 36 is disposed around an outer of the covering portion 34, for example, the bridging portion 36 can stretch out from the covering portion 34 to form a wing structure. Dimensions of the covering portion 34 can be smaller than dimensions of the opening 28, and the covering portion 34 can protrude from the housing 18 through the opening 28. Dimensions of the bridging portion 36 can be greater than the dimensions of the opening 28, and the bridging portion 36 may contact against the suspending component 40 of the housing 18 to ensure that the main body 20 does not drop out through the opening 28. The opening 28 is preferably, but not limited to, formed on the suspending component 40. In the embodiment, the waterproofing component 26 is disposed between the bridging portion 36 and the suspending component 40 of the housing 18.

Figure 2:
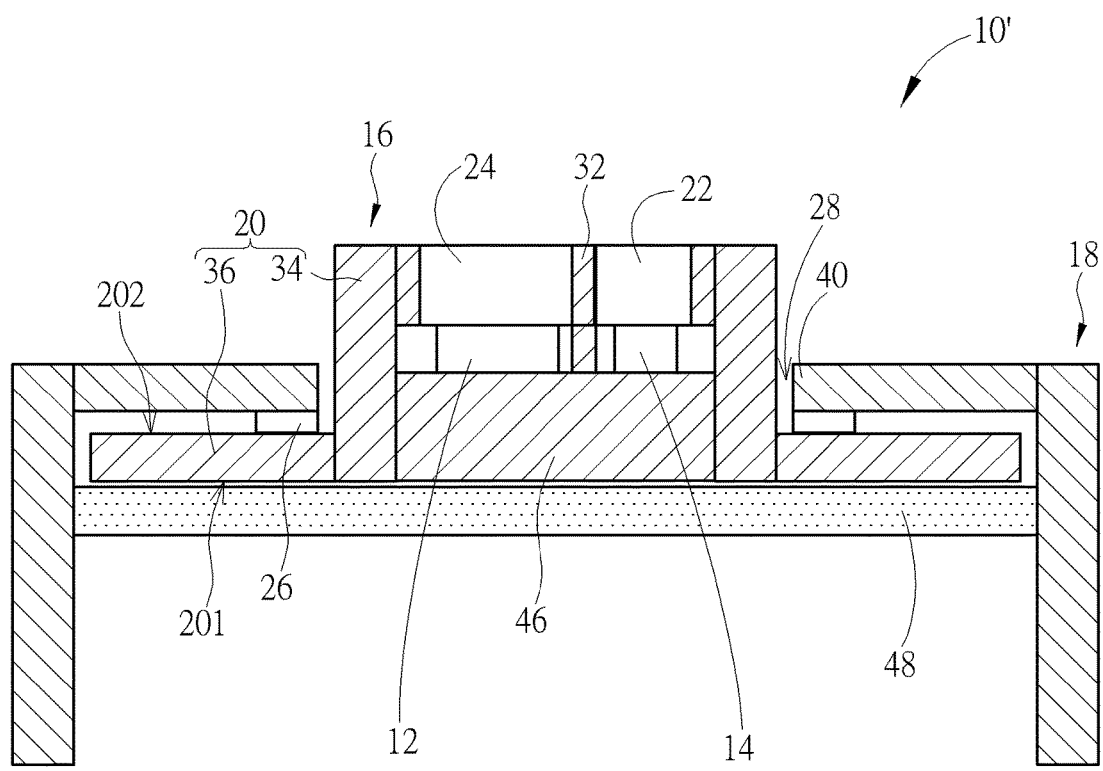
FIG. 2 is a sectional view of the optical detecting module according to a second embodiment of the present invention.
Figure 3:
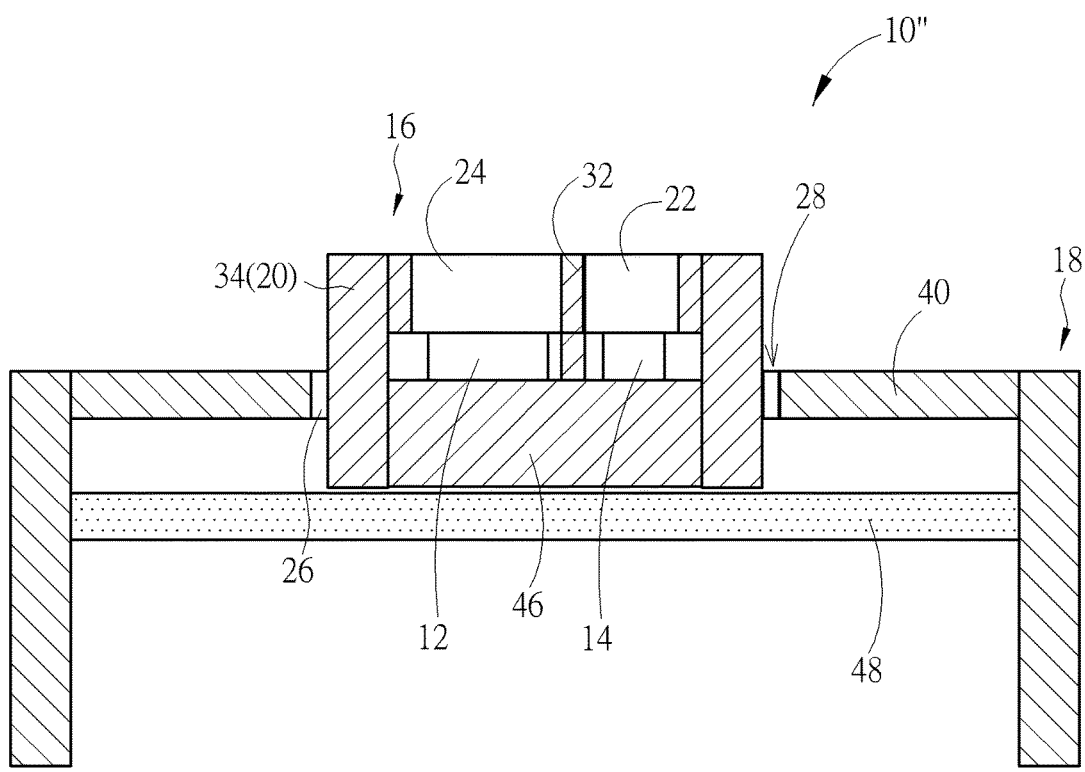
FIG. 3 is a sectional view of the optical detecting module according to a third embodiment of the present invention.

Please refer to FIG. 2 and FIG. 3. FIG. 2 is a sectional view of the optical detecting module 10' according to a second embodiment of the present invention. FIG. 3 is a sectional view of the optical detecting module 10" according to a third embodiment of the present invention. The optical detecting module 10' of the second embodiment has the optical detecting component 12 and the light source 14 integrated with the packaging structure 16 monolithically to be a modular product, which can be directly installed on the circuit board 48, and the waterproofing component 26 is preferably disposed between the bridging portion 36 and the suspending component 40 of the housing 18. Comparing to the first embodiment, the second embodiment includes a larger base 46 disposed inside the main body 20. The optical detecting component 12 and the light source 14 are heightened by the base 46 and respectively align with the light incoming unit 24 and the light emitting unit 22, and the first light transmissive unit 42 and the second light transmissive unit 44 can be omitted herein accordingly.

Difference between the optical detecting module 10" of the third embodiment and the above-mentioned embodiments is: the optical detecting module 10" has the waterproofing component 26 disposed between the covering portion 34 and the suspending component 40 of the housing 18. That is, the main body 20 of the optical detecting module 10" does not have the bridging portion 36 illustrated in the first embodiment and the second embodiment. The main body 20 of the optical detecting module 10" inserts the covering portion 34, which may be the arc shape cylinder or the polygonal cylinder, into the opening 28, and the waterproofing component 26 is disposed on the covering portion 34 and the suspending component 40 to avoid the main body 20 and the suspending component 40 from separation.

In conclusion, the present invention provides the optical detecting module matched with the housing of the wearable device for the waterproofing function. The waterproofing component of the optical detecting module is disposed between the suspending component of the housing and the covering portion/the bridging portion of the main body. The main body can be the arc shape such as the circular form or the elliptical form, and the waterproofing component is disposed around the arc shape of the main body. The main body further can be the polygonal shape such as the rectangle form, and the waterproofing component is disposed on sides of the main body accordingly. It should be mentioned that the optical detecting module has the light emitting unit and the light incoming unit disposed on a top of the main body, a distance between the top and the opening is at least greater than 0.3 mm to overcome assembly tolerance, and the optical detecting module can actually contact against the human body to detect the accurate physiological characteristics. Comparing to the prior art, the present invention effectively increase the waterproofing function of the optical detecting module applied to the wearable device, the terminals of the optical detecting component and the light source are not damaged by sweat of the human body, and the wearable device can be suitable for outdoor activity and water activity.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical detecting module with waterproofing function capable of being installed on a housing of a wearable device, the optical detecting module comprising:
   an optical detecting component;
   a light source disposed adjacent by the optical detecting component; and
   a packaging structure adapted to protect the optical detecting component and the light source by the waterproofing function, the packaging structure comprising:
      an opaque main body covering the optical detecting component and the light source, the opaque main body comprising a bridging portion at least partly overlapped by a suspending component of the housing, and the opaque main body further comprising an inner surface and an outer surface opposite to each other;
      a light emitting unit disposed on the opaque main body and facing the light source;
      a light incoming unit disposed on the opaque main body and facing the optical detecting component; and
      a waterproofing component formed on the bridging portion for filling into a gap formed between the bridging portion and the suspending component, so as to prevent exterior moisture from leaking into the gap to rust terminals of the optical detecting component and/or the light source, wherein no extra waterproofing component is formed on the housing, the optical detecting component and the light source are surrounded and covered by the inner surface of the opaque main body, and opposite sides of the waterproofing component are respectively disposed on the housing and the outer surface.

2. The optical detecting module of claim 1, wherein the packaging structure further comprises at least one blocking component disposed between the optical detecting component and the light source, and/or between the light emitting unit and the light incoming unit.

3. The optical detecting module of claim 1, wherein the opaque main body further comprises a covering portion, the optical detecting component and the light source are located inside a sunken space of the covering portion, and the bridging portion is connected to an outer of the covering portion.

4. The optical detecting module of claim 3, wherein the waterproofing component is disposed between the housing and the bridging portion, and/or between the housing and the covering portion.

5. The optical detecting module of claim 3, wherein the bridging portion stretches out from the covering portion, the packaging structure is disposed inside an opening formed on the suspending component.

6. The optical detecting module of claim 1, wherein the light emitting unit and the light incoming unit are disposed on a top of the opaque main body, and a distance between the top and an opening formed on the housing is at least greater than 0.3 mm.

7. The optical detecting module of claim 1, wherein the packaging structure further comprises a first light transmissive unit and a second light transmissive unit, the first light transmissive unit is disposed between the light source and the light emitting unit, and the second light transmissive unit is disposed between the optical detecting component and the light incoming unit.

8. The optical detecting module of claim 1, wherein the optical detecting component and the light source are respectively packed inside the packaging structure, or are integrated inside the packaging structure monolithically.

9. The optical detecting module of claim 1, wherein the opaque main body is an arc shape cylinder or a polygonal cylinder.

* * * * *